United States Patent [19]

Brooke

[11] 4,326,163

[45] Apr. 20, 1982

[54] HIGH SPEED BULK GRAIN MOISTURE MEASUREMENT APPARATUS

[76] Inventor: Robert L. Brooke, 4700 Korvett Dr., Woodbridge, Va. 22193

[21] Appl. No.: 116,711

[22] Filed: Jan. 30, 1980

[51] Int. Cl.[3] .............................................. G01R 27/04
[52] U.S. Cl. ............................................... 324/58.5 A
[58] Field of Search ............. 324/58.5 A, 58 A, 61 R; 73/73

[56] References Cited

U.S. PATENT DOCUMENTS

| | | | |
|---|---|---|---|
| 3,155,898 | 11/1964 | Chope | 324/58.5 A |
| 3,249,865 | 5/1966 | Hanken | 324/61 R |
| 3,255,411 | 6/1966 | Norwich | 324/61 R |
| 3,265,967 | 8/1966 | Heald | 324/58.5 A |

Primary Examiner—Stanley T. Krawczewicz
Attorney, Agent, or Firm—Nathan Edelberg; Robert P. Gibson

[57] ABSTRACT

Apparatus for high speed continuous monitoring of the moisture content of grain and the like is disclosed. The apparatus includes a transmitter that transmits signals having two separate frequencies through the grain that is being monitored. A receiver having an antenna placed opposite the antenna of the transmitter picks up the transmitted signals after they pass through the grain. The output of the receiver is coupled to a frequency separator which separates the signals. The two single frequency signals from the frequency separator are applied to separate inputs of a differential detector. The output, if any, from the differential detector is a measure of the moisture content of the grain.

9 Claims, 1 Drawing Figure

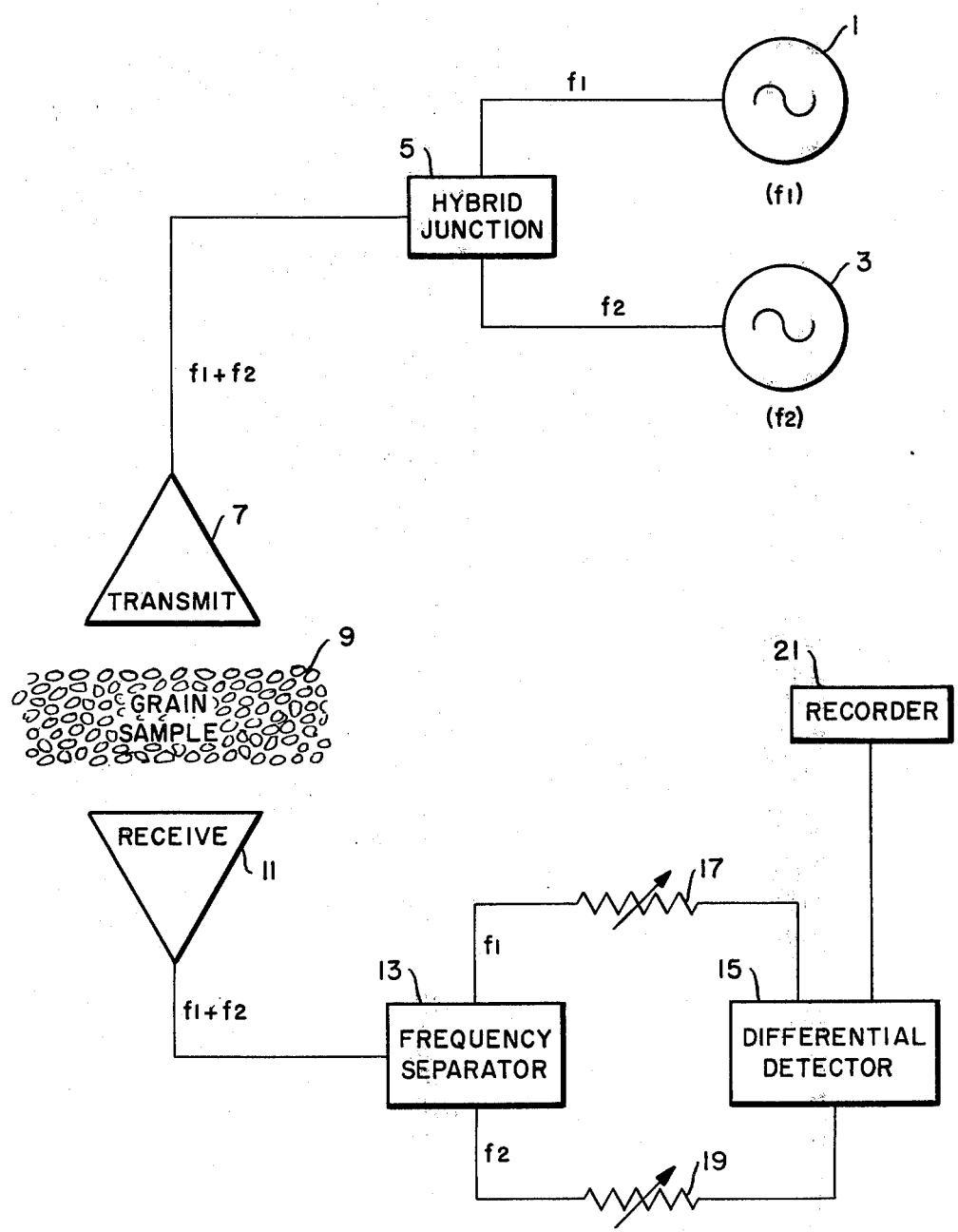

HIGH SPEED BULK GRAIN MOISTURE MEASUREMENT APPARATUS

The invention described herein may be manufactured, used, and licensed by or for the Government for Governmental purposes without the payment to me of any royalties thereon.

BACKGROUND OF THE INVENTION

This invention relates to moisture measuring apparatus, and more particularly, to apparatus for the high speed monitoring of the moisture content of grain or the like.

Excessive moisture in bulk food grain enhances the growth of poisonous molds, and stimulates oxidation which produces heat sufficient to cause spontaneous combustion. Therefore, there is a need to monitor the moisture content of bulk food grains both during storage and in transit. In one method presently used to measure the moisture content of bulk grains, small samples are collected from large storage facilities and these samples are then analyzed in a laboratory using standard physical and chemical methods. This method is extremely limited in terms of reliability of the sample. Further, this method does not afford continuous monitoring of the moisture in the bulk grain.

This invention provides for continuous monitoring of the bulk grain by means of electromagnetic radiation. During handling, bulk grain shipments usually are handled on conveyor belts or are gravity dispensed from hoppers into mail cars on tracks. In either case, it is relatively easy to pass the material through a continuous reading measurement system or port. The examination system hereof essentially comprises a transmit and receive antenna, capable of transmitting two separate frequencies through the bulk grain as it is carried by on a conveyor belt, or falls through a test port during dispensing from a storage hopper. Electromagnetic attenuation at VHF and UHF frequencies is found to be almost totally caused by the residual moisture in food grains. Systems for measuring moisture by means of electromagnetic radiation are known in the prior art. Examples of such systems are disclosed in the following U.S. Patents: U.S. Pat. No. 3,851,244 to Mounce; U.S. Pat. No. 3,694,737 to Busker et al.; U.S. Pat. No. 3,693,079 to Walker; and U.S. Pat. No. 3,498,122 to Howard.

In said U.S. Pat. No. 3,851,244 to Mounce, a rather complex microwave system is disclosed. Said U.S. Pat. No. 3,694,737 to Busker et al. discloses a microwave moisture measuring system in which the transmission path is changed by at least one-half wavelength. Said U.S. Pat. No. 3,693,079 to Walker discloses moisture measuring apparatus which utilizes a microwave signal and a penetrating signal such as x-rays or beta rays, and said U.S. Pat. No. 3,498,112 to Howard discloses a microwave system in which two separate transmitters and receivers are provided.

The apparatus of this invention also uses microwave energy to measure moisture and is primarily designed to measure the moisture content of bulk grain. The system of this invention is not a complex system. The system includes a single transmitter capable of transmitting two frequencies, a receiver, and signal processing circuitry.

SUMMARY OF THE INVENTION

This invention provides apparatus for high speed measuring of moisture; particularly, the moisture content of bulk food grains. The apparatus of this invention includes a single transmitter capable of transmitting two separate frequencies, a receiver, a frequency separator, a differential detector and a recorder and/or other metering device.

The transmitter transmits two separate frequency signals through bulk grain as it is carried on a conveyor belt or falls through a test port during dispensing from a storage hopper. The receiver is located opposite the transmitter and picks up the transmitted signals after they pass through the grain. The output of the receiver is coupled to processing circuitry which processes the output signals from the receiver to provide an output signal that is a measure of the moisture content of the grain.

BRIEF DESCRIPTION OF THE DRAWING

A full and complete understanding of the invention can be obtained from the following detailed description when read in conjunction with the annexed drawing in which the single FIGURE illustrates a preferred embodiment of the invention.

DETAILED DESCRIPTION OF THE INVENTION

The single FIGURE illustrates a preferred embodiment of the high speed moisture measuring system of this invention. As shown in the drawing, the preferred embodiment includes a first oscillator 1 which generates a signal having a frequency at (f1) and a second oscillator 3 which generates a signal having a frequency (f2). The (f1) signal from oscillator 1 is applied to a first input of the hybrid junction 5 and the (f2) signal from oscillator 3 is applied to the second input of hybrid junction 5. The output of hybrid junction 5 (f1+f2) is applied to the input of the transmitter 7.

Transmitter 7, which of course includes an antenna not specifically shown, transmits the (f1+f2) signal through the grain sample. Grain sample 9 may be passing past transmitter 7 on a conveyor belt for example or may be falling part transmitter 7 as it is dispensed from a storage hopper, for example.

A receiver 11, which also includes an antenna not specifically shown, is located opposite transmitter 7 and picks up the transmitted signals from transmitter 7 after the signals pass through grain sample 9. The output from receiver 11 (f1+f2) is applied to a frequency separator 13. Frequency separator 13 separates the signals from receiver 11 into two separate signals, one having the frequency (f1) and the other having the frequency (f2). The (f1) signals, which are present on one of two outputs of frequency separator 13, are coupled to one of two inputs of the differential detector 15 through a variable resistor 17. The (f2) signals, which are present on the other of the two inputs of frequency separator 13, are coupled to the second one of the two inputs of differential detector 15 through the variable resistor 19.

Differential detector 15 compares the amplitude of the (f1) and (f2) signals and produces an output signal indicative of the difference in amplitude of the two signals. If the two signals are equal in amplitude, the output from differential detector 15 is zero. The output of differential detector 15, which is measure of the moisture content of grain sample 7 is applied to a recorder 21. Recorder 21 records the output signals from differential 15 and therefore provides a record of the moisture content of bulk grain sample 9 as the grain sample passes between transmitter 7 and receiver 11. Recorder 21 may be any type of recorder, for example a chart recorder. With a chart recorder, an immediate visual record of the moisture content of grain sample 9 is obtained. In addition to recorder 21, a meter may be connected to the output of differential detector 15 or if no permanent record is desired a meter alone can be used.

In operation, the apparatus is first energized without any grain sample passing between transmitter 7 and receiver 11. The variable resistors 17 and 19 are then adjusted until the output of differential detector 15 is zero. The grain is then passed between transmitter 7 and receiver 11. The amplitude of the output signal from differential detector 15, which is the difference in the amplitude of the two signals, is directly proportional to the moisture content of the grain passing between the two antennas.

The derivative of signal transmission with respect to frequency is the gauge for measurement of moisture.

% Moisture = K [(Amplitude (f1) − Amplitude (f2))/(f1 − f2)]

This gauge is insensitive to the quantity of grain, but care must be taken to ensure sufficient grain is being measured to produce a difference in amplitudes which is well above receiver noise. In addition, care must be taken to ensure that the signal at the higher frequency, which is subject to much higher attenuation, is above the noise threshold of it's portion of the Differential Detector.

The simplest frequencies to use are in the range of 50 to 1000 mega Hertz with one frequency selected near the low end, for example 500, and one selected near the high end, for example the 1000 mega Hertz frequency. Frequencies outside this range can be used but may require cumbersome antennas or result in excessive attenuation.

This invention lends itself to continuous monitoring of bulk grain shipments and with proper calibration, to determine the constant of proportionality (K), it can be very accurate even with high flow rates of grain. Calibration is conveniently accomplished by placing sealed plastic containers having grains with a known moisture content between transmitter 7 and receiver 11. Calibrated meters can give instantaneous readings, especially where the acceptable "dry" calibrated range is marked with a green background color, and the unacceptable excessive moisture range is marked with a red background color. A series of such monitoring devices with a recorder attached to the differential detector output, will provide a permanent record of the condition and moisture content of bulk grain during transit as it proceeds from the farm to final destination. This would be especially useful where the U.S. Government is responsible for ensuring the quality or condition of large grain shipments on the international market.

From the foregoing description it is apparent that this invention provides a simple, effective and inexpensive method for measuring the moisture content of bulk grain. While the invention has been described with reference to a specific embodiment, it will be apparent to those skilled in the art that various changes and modifications can be made to the specific embodiment shown and described without departing from the spirit and scope of the invention as set forth in the claims.

What is claimed is:

1. Apparatus for measuring the moisture content of bulk grains comprising:

a first oscillator generating signals having a frequency (f1);

a second oscillator generating signals having a frequency (f2);

transmitter means having an input coupled to said first and second oscillators and having an output adapted to produce output signals at a frequency (f1+f2);

receiver means adapted to produce said (f1+f2) signals at its output in response to said transmitter output signals, said receiver means being located opposite said transmitter such that said bulk grain whose moisture content is being measured passes between said transmitter means and said receiver means, said output signals from said transmitter means passing through said bulk grain to said receiver means; and means coupled to said receiver output for separating said (f1+f2) signals into two separate signals and for immediately producing an output signal directly related to the difference in amplitude between said two separate signals.

2. Apparatus for measuring the moisture content of bulk grain as defined in claim 1 wherein said input of said transmitter means is coupled to said first and second oscillator through a hybrid coupler.

3. Apparatus for measuring the moisture content of bulk grain as defined in claim 2 wherein said means for separating said (f1+f2) signals into two separate signals and for producing an output signal directly related to the difference in amplitude between said two signals comprises: a frequency separator having an input coupled to said output of said receiver and a first output and a second output, and a differential detector having a first input coupled to said first output of said frequency separator, a second input coupled to said second output of said frequency separator, and an output, with said signal directly related to the difference between the amplitude of said two separate signals appearing on said output of said differential detector.

4. Apparatus for measuring the moisture content of bulk grain as defined in claim 3 wherein said first input of said differential detector is coupled to said first output of said frequency separator through a first variable resistor and said second input of said differential detector is coupled to said second output of said frequency separator through a second variable resistor.

5. Apparatus for measuring the moisture content of bulk grain as defined in claim 3 wherein said output of said differential detector is coupled to a recorder.

6. Apparatus for measuring the moisture content of bulk grain as defined in claim 4 wherein said output of said differential detector is coupled to a recorder.

7. Apparatus for measuring the moisture content of bulk grain as defined in claim 5 wherein said frequency separator separates said (f1+f2) signals into a first signal having a frequency (f1) and a second signal having a frequency (f2).

8. Apparatus for measuring the moisture content of bulk grain as defined in claim 1 wherein said bulk grain is continuously flowing between said transmitter means and said receiver means.

9. Apparatus for measuring the moisture content of bulk grain as defined in claim 7 wherein said bulk grain is continuously flowing between said transmitter means and said receiver means.

* * * * *